US006274382B1

(12) United States Patent
Treiber

(10) Patent No.: US 6,274,382 B1
(45) Date of Patent: Aug. 14, 2001

(54) METHOD AND REAGENT FOR THE INTERFERENCE-FREE DETERMINATION OF IRON

(75) Inventor: Wolfgang Treiber, Weilheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/296,920

(22) Filed: Apr. 22, 1999

(30) Foreign Application Priority Data

Apr. 22, 1998 (DE) ............................................... 198 17 963

(51) Int. Cl.⁷ ..................................................... G01N 33/20
(52) U.S. Cl. .................................. 436/74; 436/8; 436/73; 436/81; 436/84; 436/164; 436/166
(58) Field of Search ................................... 436/8, 73, 74, 436/81, 82, 84, 164, 166

(56) References Cited

U.S. PATENT DOCUMENTS

| | | | |
|---|---|---|---|
| 3,887,332 | * 6/1975 | Takase et al. ........................... | 436/17 |
| 3,925,020 | * 12/1975 | Ogawa et al. ........................... | 436/57 |
| 4,308,027 | * 12/1981 | Ceriotti ................................... | 436/74 |
| 4,588,695 | * 5/1986 | Takano et al. ........................... | 436/87 |
| 4,961,970 | * 10/1990 | Siedel et al. ............................ | 436/84 |
| 5,219,760 | * 6/1993 | Herrmann et al. ...................... | 436/84 |
| 5,763,281 | * 6/1998 | Weisheit et al. ........................ | 436/74 |
| 5,925,570 | * 7/1999 | Nishidate et al. ....................... | 436/74 |

FOREIGN PATENT DOCUMENTS 0 306 859 A1   3/1989   (EP) .
0 343 592 A2   11/1989  (EP) .

* cited by examiner

Primary Examiner—Maureen M. Wallenhorst

(57) ABSTRACT

Method and reagent for the determination of iron in a biological sample in which the bound iron is released, the released iron is reduced to $Fe^{2+}$, a color reagent solution is added and the color complex that is formed is measured photometrically, characterized in that a water-soluble EDTA-complexing compound in particular an indium and/or scandium salt is added to the sample.

16 Claims, 1 Drawing Sheet

METHOD AND REAGENT FOR THE INTERFERENCE-FREE DETERMINATION OF IRON

BACKGROUND AND SUMMARY OF THE INVENTION

The invention concerns a method for the interference-free determination of iron in biological samples, in particular in serum in which bound iron is released, the released iron is reduced to $Fe^{2+}$, a color reagent solution is added and a color complex that forms is measured photometrically and it also concerns a combination of reagents which is suitable for the interference-free determination of iron especially in the presence of high amounts of EDTA.

Disorders of iron metabolism, in particular iron deficiency and disorders of iron absorption are widespread especially in the female population. Hence the detection of iron in body fluids and in particular in serum is one of the standard determinations in medical analytics. Iron is provided with the diet and absorbed via the intestinal mucosa. Bound to transferrin in a trivalent state, it is then transported to the bone marrow where it is mainly incorporated into haemoglobin. Anaemic symptoms occur if too little iron is absorbed.

The determination of iron in serum is one of the most frequently carried out trace element analyses in clinical diagnostics. With regard to the release of iron from transferrin, two basic test variants for the determination are known. In the one case iron can be detached by adding detergent mixtures (e.g. EP 0 130 537), guanidinium chloride (e.g. EP 0 343 592) or for example urea-containing denaturing agents (e.g. DE 44 01 754) at a weakly acidic pH. On the other hand, iron can be detached from transferrin in a strongly acidic medium, in particular at a pH value of ca. 2.5 or lower (Clin. Chem. vol. 26 (1980), 327–331).

However, a disadvantage of the said test principles is that the presence of EDTA which is often present in biological samples, for example as a result of corresponding pretreatments, causes interference. The reason is that EDTA is able to form complexes with iron and the iron bound in this manner is therefore not available for the formation of a color complex. This can lead to false-negative iron values especially with EDTA plasma as a sample material. Furthermore, there is a risk that when such determinations are carried out on automated analysers, there is a carry-over of EDTA from other test liquids due to unavoidable pipetting or stirring devices or inadequately cleaned reaction vessels which results in a reduced color signal and thus to a reduced recovery of the iron.

In order to eliminate this disadvantage, zinc (II) salts are added in test variants which release the iron by a suitable denaturing agent. The EDTA contamination is masked by $Zn^{2+}$ ions which avoids interference due to reactions of EDTA with $Fe^{2+}$ ions.

In contrast the addition of zinc(II) salts does not eliminate interference caused by EDTA in test variants in which iron is released in a strongly acidic medium. Furthermore it has turned out that in the presence of high salt concentrations (ca. 4 mol/l) and/or high detergent concentrations (ca. 7%) the reagent solution is observed to "creep out" of the reagent bottles leading for example to destruction of bar code labels and corrosion of metal components in automated analysers.

Consequently the object of the present invention is to provide a method and reagent for the determination of iron in biological sample material which is suitable for the release of iron at strongly acidic pH values and/or in solutions with high salt or detergent concentrations in which no essential interference occurs in the presence of EDTA and reduced recovery of iron caused by EDTA is avoided.

The object is achieved by a method for the determination of iron in a biological sample in which the bound iron is released, the released iron is reduced to $Fe^{2+}$, a color reagent solution is added and the color complex that is formed is measured photometrically, wherein the sample is contacted with a water-soluble salt composed of metal cations of the IIIrd main group and subgroup (III a+b) of the periodic system of the elements such as scandium, indium, lanthanum or gallium. Indium and/or scandium salts are preferred according to the invention. The counterion of the salts to be added according to the invention is uncritical provided water-soluble salts are formed. In particular divalent or trivalent cations and the following acidic residues have proven to be suitable: halogenides, phosphates, nitrates, sulfites and sulfates, of which chlorides and sulfates are preferred.

The concentration of the salts according to the invention of the IIIrd main group or subgroup in the reagent solution (final concentration in the test) is at least about 0.1 mmol/l, a range between about 0.1 and 50 mmol/l is preferred and a concentration between about 1 and 20 mmol/l is particularly preferred.

DETAILED DESCRIPTION OF THE INVENTION

Figure 1:
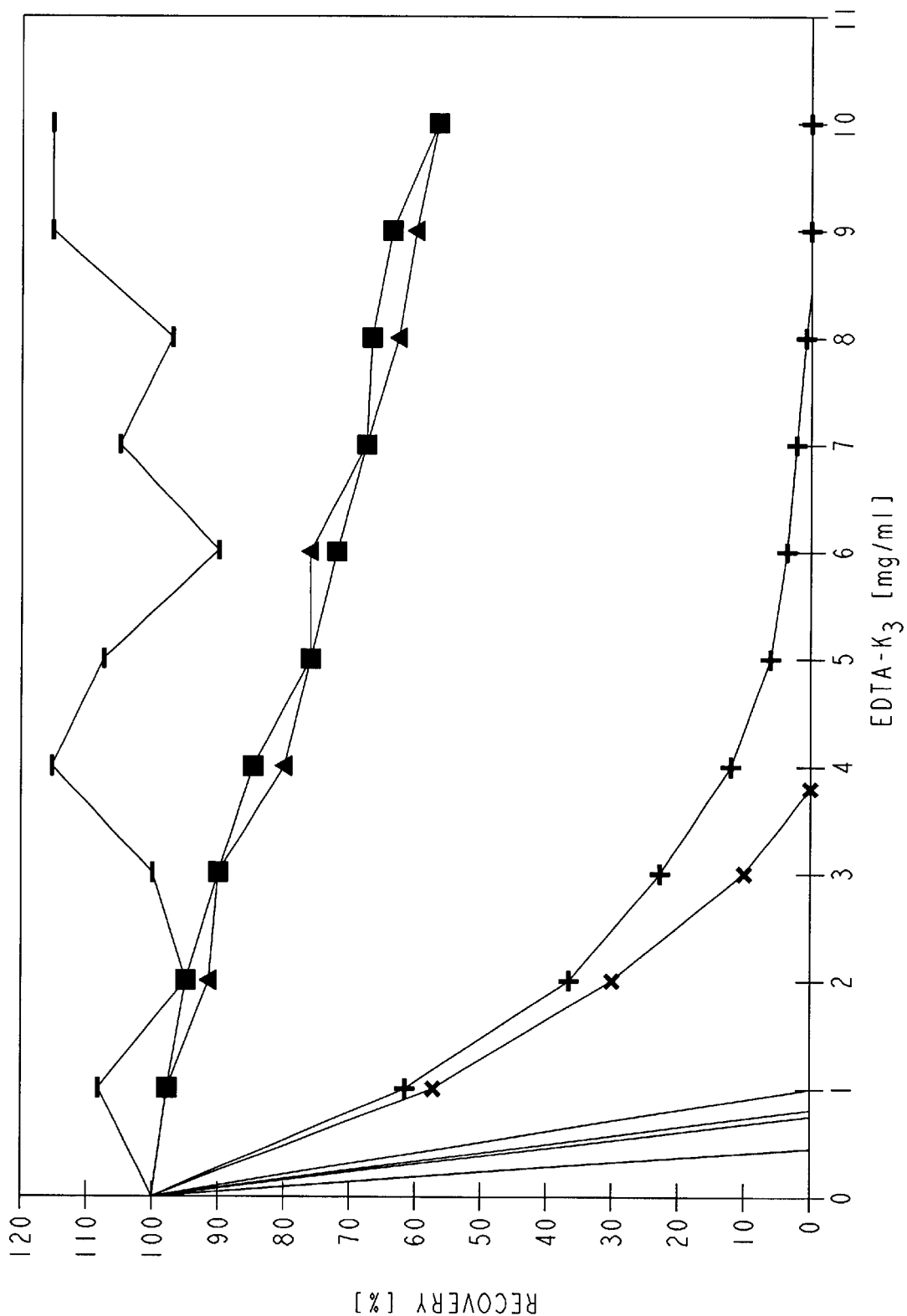
FIG. 1 is a graph showing the percentage recovery of iron in the presence of 0 to 10 mg/ml EDTA tripotassium salt.

In the method according to the invention the bound iron can in principle be released by measures known to a person skilled in the art such as by adding suitable detergent mixtures (e.g. EP 0 130 537, DE 27 24 757 or DE 37 29 502) or a denaturing agent such as guanidinium chloride (e.g. EP 0 343 592) usually at pH values between 3 and 6 or at strongly acidic pH values where an iron-releasing substance is not added. According to the invention a pH value between 0 and 3 has proven to be advantageous when the iron is detached in a strongly acidic medium.

In order to carry out the method according to the invention the sample or the reagent mixture is preferably kept in a weak and strongly acidic range, particularly preferably in the range between pH 0 and pH 6. Compounds are suitable as buffer substances which have a pk value of 2.5 to 6 and which do not or only weakly complex iron. Acetate, citrate, phosphate or succinate buffers are for example suitable. A further preferred variant for releasing the iron is firstly to adjust an acidic pH value, particularly preferably pH 3 to pH 6, and subsequently to rebuffer to a pH value which gives an optimal color yield with the color system selected for the detection of iron. Suitable pH values for this are known to a person skilled in the art, for example from Fielding, Methods in Hematology 1 (Iron), 15–49 (1980). It is particularly preferable for the method according to the invention when the bound iron is released in a strong acidic medium, preferably between pH 0 and 3, and an EDTA-complexing substance is added. Suitable EDTA-complexing substances are in particular salts composed of a divalent or trivalent cation of groups IIIa, IIIb IVa, VIII of the periodic system and/or lanthanides such as scandium, indium, zirconium, nickel, ytterbium and lutetium, of which scandium and/or indium are preferred.

Acetate or citrate buffer is preferably used as the buffer substance. The buffer is preferably used at a concentration of 20 to 500 mmol/l, in particular in a range of 50 to 250 mmol/l. It is especially preferred when the buffer solution contains ca. 200 mmol/l citric acid. The buffer substance can be contained in a first solution of the iron test according to the invention which can additionally contain a denaturing agent and optionally a fatty alcohol polyglycol ether. In addition the other solutions or the other solution of the iron test according to the invention can also be buffered and additional auxiliary substances for stabilization and/or to eliminate or reduce undesired reactions can be added. Thus for example interference by lipaemic biological samples can be avoided by adding fatty alcohol polyglycol ethers or alkylpolyethylene glycol ethers (DE 44 01 754). A further advantageous embodiment of the method according to the invention is when thiourea is added to the reagent especially preferably between 10 and 200 mM. This can eliminate especially copper interference.

In order to determine iron a reducing agent such as ascorbic acid, dithionite or hydroxylamine is added in a known manner to the sample solution in order to reduce the released iron present in a trivalent form to the divalent form. The reducing agent can be added to the first solution together with the optionally used denaturing agent as well as to the second solution which also contains the suitable color system for the detection of iron. However, the reducing agent is preferably added to the second solution. Furthermore it is preferable if the reagent additionally contains a substance which stabilizes the reducing agent such as a suitable preservative (e.g. Germall II).

Color systems for the detection of iron are for example described in EP 0 228 060, Clin. Biochem. 14 (1981), 311–315 and Clin. Chem. 23 (1979), 234–240. Complexing agents of the ferroin type are particularly suitable which generate a dye with iron which can be evaluated photometrically. Suitable substances are bathophenanthroline and Ferrozine (3'(2'-pyridyl)-5,6-diphenyl-1,2,4-triazine-sulfonic acid disodium salt or 3'(2'-pyridyl)-5,6-bis(4-phenyl-sulfonic acid)-1,2,4-triazine monosodium salt). In this process the formation of dye is proportional to the content of iron in the sample and can be evaluated photometrically in a known manner.

The invention succeeds for the first time in avoiding interference by EDTA in the photometric determination of iron and also especially in strongly acidic reagent solutions.

Hence a further subject matter of the invention is the use of water-soluble indium and/or scandium salts to prevent interference caused by the presence of EDTA in the photometric determination of iron in a biological sample.

The effectiveness of the reagent in avoiding EDTA interference can be checked photometrically at a sample/reagent ratio of 1:5 to 1:25, preferably of 1:10 to 1:15. A recovery of iron with only a ca. 10% deviation was achievable. The measurement is usually carried out at a temperature of ca. 37° C. and at a wavelength of ca. 570–580 nm using a cuvette with a light path of 1 cm against the reagent solution as a blank.

A further subject matter of the invention is a combination of reagents for the determination of iron in a biological sample characterized by a first reagent which is able to release bound iron and contains at least 0.1 mmol/l of a water-soluble salt composed of a metal cation of the IIIrd main group and/or subgroup, preferably of an indium and/or scandium salt and separate therefrom a second reagent containing 0.5 to 50 mmol/l dye which are present in the form of aqueous solutions or as dry mixtures that are suitable for their preparation. Both reagents or only the first reagent can additionally contain 20 to 500 mmol/l buffer substance.

In particular the first reagent can additionally contain further auxiliary substances such as a suitable detergent for avoiding lipaemic interference preferably about 1% to 10% (w/v) alkylpolyethylene glycol ether (e.g. Genapol X-80: isotridecylpoly(ethylene glycol ether)n, n=8) or to avoid interference caused by copper in which case 10 to 200 mM thiourea is preferred.

The second reagent can additionally contain a reducing agent such as ascorbic acid, dithionite or hydroxylamine at a concentration of 20 to 200 mmol/l. The second reagent can optionally contain a substance or mixture of substances which stabilizes the reducing agent such as the commercially available substances Germall II, Germall 115, Oxaban A or Oxaban E at a concentration of 0.5 to 6.0 g/l, preferably of 1 to 3 g/l. In addition it is also possible to not add the reducing agent until shortly before using the liquid reagent.

The two reagents can be present in the form of aqueous solutions or as suitable dry mixtures (lyophilisates) for their preparation.

The reagent combination is additionally characterized by a surprisingly high stability. Thus it has turned out that the reagent after storage for 24 hours at 42° C. or 3 weeks at 35° C. (corresponding to a stress model for 18 months real time at 2–8° C.) can be used for the interference-free determination of iron without any loss of quality or activity.

Figure legends:

FIG. 1:

Percentage recovery of iron in the presence of 0 to 10 mg/ml EDTA tripotassium salt; sample: human serum pool ca. 77 µg/dl iron; following additives —■—10 mM indium sulfate, —▲—10 mM scandium sulfate, —□—20 mM nickel sulfate, —+—10 mM ytterbium sulfate, —◊—10 mM zirconium sulfate, —✳—10 mM lutetium sulfate; and other curves: without additives or ineffective additives.

The invention is further elucidated by the following examples.

Example 1

The following reagents are used to determine iron in serum:

| Reagent 1: | 200 mmol/l | citric acid |
| | 100 mmol/l | thiourea |
| | 7% (w/v) | alkylpolyethylene glycol ether |
| | 10 mmol/l | indium (III) chloride |
| Reagent 2: | 150 mmol/l | sodium ascorbate |
| | 6 mmol/l | 3'(2'-pyridyl)-5,6-bis(4-phenylsulfonic acid)-1,2,3-triazine monosodium salt |

The determinations were carried out on a Hitachi 717 automated analyser, Boehringer Mannheim GmbH at a measuring temperature of 37° C. The measurement was carried out at a wavelength of 570 nm against the reference wavelength of 700 nm. The difference between the measurement wavelength and reference wavelength was evaluated.

20 μl of a serum sample and 250 μl reagent 1 were pipetted into a cuvette and incubated at 37° C. after mixing. After 5 minutes a first absorbance was measured. Subsequently 50 μl reagent 2 was added by pipette, mixed, incubated for a further 5 minutes and then a second absorbance was measured. The evaluation was carried out by determining the difference between the two absorbance values.

A blank using 0.9% saline solution as a sample and a calibrator with a known content of iron were analysed in the same manner. A linear calibration curve was established from these two samples from which readings were subsequently taken for the known samples.

Results:

3 mg/ml EDTA-$K_3$ was added to a human serum (typical concentration of an EDTA plasma) and used as a sample. The unspiked human serum pool was measured as a reference value and the recovery of the spiked sample relative to the unspiked sample was calculated.

TABLE 1

| Addition to reagent 1 | Recovery |
|---|---|
| without addition | −2.8% |
| 10 mmol/l indium sulfate | 89.4% |
| 10 mmol/l scandium sulfate | 88.9% |
| 10 mmol/l lutetium sulfate | 8.8% |
| 10 mmol/l ytterbium sulfate | 22.0% |
| 10 mmol/l nickel sulfate | 79.8% |
| 10 mmol/l zirconium sulfate | 16.7% |

What is claimed is:

1. In a method for the determination of iron in a test solution having a pH value between 0 and 3 of a biological sample wherein iron bound to transferrin is released and reduced to $Fe^{+2}$ and wherein a color reagent is added and a color complex thus formed measured photometrically, the improvement comprising adding to said test solution a water-soluble salt comprising a metal cation selected from the group consisting of Groups IIIa and IIIb of the periodic system, said water-soluble salt being added in an amount sufficient to avoid interference from EDTA.

2. The method of claim 1, wherein the concentration of said water-soluble salt in said test solution is between 0.1 and 50 mmol/l.

3. The method of claim 1, wherein said metal cation is indium or scandium.

4. A method for the determination of iron in a biological sample containing transferrin comprising:

(a) combining said sample with a buffer to form a test solution having a pH value of between 0 and 3, said buffer being at a pH suitable for releasing iron bound to said transferrin, (b) adding to said test solution a water-soluble salt comprising a metal cation selected from the group consisting of Groups IIIa and IIIb of the periodic system, wherein said metal cation is added in an amount sufficient to avoid interference from EDTA, (c) adding an agent to reduce the iron released from said transferrin, (d) adding a color reagent to form a color complex with the reduced iron, and (e) measuring any resulting color complex photometrically as an indication of the iron present in the sample.

5. The method of claim 4, wherein the concentration of said water-soluble salt in said test solution is between 0.1 and 50 mmol/l.

6. The method of claim 4, wherein said metal cation is indium or scandium.

7. A combination of reagents for the determination of iron in a biological sample containing transferrin, said combination comprising:

(a) a first reagent having a pH value between 0 and 3 comprising an agent for releasing iron bound to said transferrin and about 0.1 mmol/l to 50 mmol/l of a water-soluble salt in an amount sufficient to avoid interference from EDTA, wherein said water-soluble salt comprises a metal cation selected from the group consisting of Groups IIIa and IIIb of the periodic system, and (b) a second reagent comprising about 0.5 to 50 mmol/l of a color reagent suitable for forming a color complex with iron, said first and second reagents being in the form of aqueous solutions or dry mixtures suitable for preparation of aqueous solutions.

8. The combination of reagents of claim 7, wherein said first reagent further comprises about 1% to 10% (w/v) of an alkylpolyethylene glycol ether.

9. The combination of reagents of claim 7, wherein said second reagent further comprises about 20 to 200 mmol/l of a reducing agent.

10. In a method for the determination of iron in a test solution of a biological sample wherein iron bound to transferrin is released and reduced to $Fe^{+2}$ and wherein a color reagent is added and a color complex thus formed measured photometrically, the improvement comprising adding to said test solution a water-soluble EDTA-complexing compound, said compound being added in an amount sufficient to avoid interference from EDTA with $Fe^{+2}$ and the pH value of said test solution being below 3.

11. A method for the determination of iron in a biological sample containing transferrin comprising:

combining said sample with a buffer to form a test solution having a salt concentration of at least 4 mol/l and a pH value of between 0 and 3, said buffer being at a pH suitable for releasing iron bound to said transferrin, adding to said test solution a water-soluble salt comprising a metal cation selected from the group consisting of Groups IIIa and IIIb of the periodic system, wherein said metal cation is added in an amount sufficient to avoid interference from EDTA, adding an agent to reduce the iron released from said transferrin, adding a color reagent to form a color complex with the reduced iron, and measuring any resulting color complex photometrically as an indication of the iron present in the sample.

12. The method of claim 11, wherein the concentration of the water-soluble salt in said solution is between 0.1 and 50 mmol/l.

13. The method of claim 11, wherein the metal cation is indium or scandium.

14. A method for the determination of iron in a biological sample containing transferrin comprising:

combining said sample with a buffer to form a test solution having a detergent concentration of at least 7% (w/v) and a pH value of between 0 and 3, said buffer being at a pH suitable for releasing iron bound to said transferrin, adding to said test solution a water-soluble salt comprising a metal cation selected from the group consisting of Groups IIIa and IIIb of the periodic system, wherein said metal cation is added in an amount sufficient to avoid interference from EDTA, adding an agent to reduce the iron released from said transferrin, adding a color reagent to form a color complex with the reduced iron, and measuring any resulting color complex photometrically as an indication of the iron present in the sample.

15. The method of claim 14, wherein the concentration of the water-soluble salt in said solution is between 0.1 and 50 mmol/l.

16. The method of claim 14, wherein the metal cation is indium or scandium.

* * * * *